United States Patent
Cholet et al.

(10) Patent No.: US 10,617,781 B2
(45) Date of Patent: Apr. 14, 2020

(54) DEVICE FOR CATALYTIC DIFFUSION OF A FRAGRANCE

(71) Applicant: PRODUITS BERGER, Bourgtheroulde-infreville (FR)

(72) Inventors: Vincent Cholet, Surtauville (FR); Corinne Gerard, Incarville (FR)

(73) Assignee: PRODUITS BERGER, Bourgtheroulde-Infreville (FR)

( * ) Notice: Subject to any disclaimer, the term of this patent is extended or adjusted under 35 U.S.C. 154(b) by 17 days.

(21) Appl. No.: 15/553,417

(22) PCT Filed: Nov. 30, 2015

(86) PCT No.: PCT/FR2015/053267
§ 371 (c)(1),
(2) Date: Aug. 24, 2017

(87) PCT Pub. No.: WO2016/135388
PCT Pub. Date: Sep. 1, 2016

(65) Prior Publication Data
US 2018/0093004 A1 Apr. 5, 2018

(30) Foreign Application Priority Data
Feb. 24, 2015 (FR) ..................... 15 51583

(51) Int. Cl.
*A61L 9/03* (2006.01)
*F23D 3/00* (2006.01)
(Continued)

(52) U.S. Cl.
CPC .......... *A61L 9/037* (2013.01); *B65D 41/0428* (2013.01); *B65D 41/0442* (2013.01);
(Continued)

(58) Field of Classification Search
CPC . A61L 9/037; B65D 41/0428; B65D 41/0442; B65D 51/18; B65D 2251/0015;
(Continued)

(56) References Cited

U.S. PATENT DOCUMENTS

2007/0153519 A1 7/2007 Sexton et al.
2009/0291400 A1 11/2009 Levy
2012/0276489 A1 11/2012 Fang

FOREIGN PATENT DOCUMENTS

| FR | 2166653 A5 | 8/1973 |
| FR | 2821749 A1 | 9/2002 |
| JP | 2013-111199 A | 6/2013 |

OTHER PUBLICATIONS

English-language machine translation of FR2166653 (Year: 1973).*
(Continued)

*Primary Examiner* — Timothy C Cleveland
(74) *Attorney, Agent, or Firm* — Kenealy Vaidya LLP

(57) ABSTRACT

Some embodiments are directed to a device for catalytically diffusing a fragrance or active substances, wherein the device includes a bottle with a base, and containing a liquid including a fragrance; a catalytic combustion burner mounted on the base; a capillary wick attached to the burner and partially submerged in the liquid; and a closing cap removably mounted on the base and covering the burner. The cap includes a sealing means bearing against a periphery of a top of the base.

10 Claims, 4 Drawing Sheets

(51) Int. Cl.
    *B65D 41/04*     (2006.01)
    *B65D 51/18*     (2006.01)
(52) U.S. Cl.
    CPC ............... *B65D 51/18* (2013.01); *F23D 3/00* (2013.01); *B65D 2251/0015* (2013.01); *B65D 2251/0078* (2013.01)
(58) Field of Classification Search
    CPC ..... B65D 2251/0078; F23D 3/00; F23D 3/02; F23D 3/24
    See application file for complete search history.

(56) References Cited

OTHER PUBLICATIONS

International Search Report and Written Opinion for PCT Patent App. No. PCT/FR2015/053267 (dated Apr. 13, 2016) with English language translation of the ISR.
Preliminary Search Report from French Patent App. No. 1551583 (dated Aug. 7, 2015).

* cited by examiner

DEVICE FOR CATALYTIC DIFFUSION OF A FRAGRANCE

CROSS REFERENCE TO RELATED APPLICATIONS

This application is a national phase filing under 35 C.F.R. § 371 of and claims priority to PCT Patent Application No. PCT/FR2015/053267, filed on Nov. 30, 2015, which claims the priority benefit under 35 U.S.C. § 119 of French Patent Application No. 1551583, filed on Feb. 24, 2015, the contents of each of which are hereby incorporated in their entireties by reference.

BACKGROUND

Some embodiments relate to the field of ambient adjustment.

More particularly, some embodiments relate to a mobile device for the diffusion of a fragrance or active substances (such as for example, insecticides) by catalysis.

The use of devices for the diffusion of a fragrance by catalysis, also known as catalytic combustion lamps, for diffusing an ambient fragrance or active substance is known. Conventionally such lamps include:
- a container or bottle suitable for receiving a fragranced liquid material or containing an active substance;
- a catalytic combustion burner including a wick through which the liquid material is raised by capillarity;
- a support assembled with the burner so that it can be positioned on the base;
- a metal base for positioning the burner, which may be of one piece with the container;
- a pierced protection which, once fitted on the lamp, provides protection against access to the burner and creates ventilation around the burner; and
- a snuffer positioned to rest on the burner and the base, whereby catalytic combustion may be stopped.

Such lamps thus diffuse an environmental fragrance or an active substance by catalysis of the liquid material coming up the wick by capillarity.

However these lamps have the disadvantage that they are difficult to transport when they are filled with liquid material, which is unsatisfactory. In fact, the snuffer positioned to rest on the burner and the base does not ensure that the device is leaktight, and because the base has a hole to place the lamp at atmospheric pressure and the positioning of the burner support on the base creates clearance fit, liquid material may accumulate in the snuffer and flow between the snuffer and the base and then spill along the base and the lamp. As this material may be flammable, such a possibility cannot therefore be envisaged for safety reasons, as well as from the point of view of cleanliness.

Furthermore such lamps for the diffusion of a fragrance or active substance by catalysis are not transportable, because once filled they must be positioned on a substantially flat horizontal surface so as not to spill the liquid material which they contain. They cannot therefore obviously be laid down, otherwise the liquid contained would spill, which is unsatisfactory.

SUMMARY

Some embodiments has in particular the object of at least partly overcoming the disadvantages of the prior art.

In particular, one object of at least one embodiment is to provide a device for diffusion of a fragrance or active substance by catalysis which is relatively leaktight during its transport (only because the device is not leaktight when in operation) and which offers satisfactory safety for a user.

Another object of at least one embodiment is to provide such a device which can be easily transported once filled without presenting any risk of spillage of the liquid and which can be used wholly safely after transport without any liquid spilling during use.

Another object is to provide such a device which is simple to use and inexpensive to implement.

These objects, and others which will be apparent below, are accomplished through a device for the diffusion of a fragrance or active substance by catalysis including a bottle having a base and containing a liquid including a fragrance or an active substance, a catalytic combustion burner mounted on the base, a capillary wick attached to the burner and partly immersed in the liquid, and a closing cap removably mounted on the base and covering the burner, the cap including sealing means bearing against a periphery of a top of the base.

Thus the fact of providing sealing means bearing on a periphery of a top of the base has the effect that any spillage of liquid including a fragrance or an active substance between the base and the burner remains confined in the cap and then is returned to the bottle once the device is restored to a vertical operating position. Thus, when the cap is opened, there is no residual liquid on the outside of the base and of the burner, thus ensuring that they are clean, and avoiding any risk when the device is lighted up.

Advantageously, but optionally, the device according to some embodiments has at least one of the following additional technical characteristics:
- the sealing means include a seal having a shape which complements a periphery of a top of the base;
- the cap includes a housing for receiving and holding the seal;
- the sealing means include a sealing lip bearing against a periphery of a top of the base;
- the cap includes a cover made of heat-resistant material;
- the cap includes an insert fitted into the cover of heat-resistant material;
- the insert is hollow and extends from below a burner head toward the bottle;
- the envelope includes a shouldered rim;
- the cap includes a sealing element between an upper surface of the insert and the cover of heat-resistant material; and,
- the device further includes a burner support positioned between the burner and the base.

BRIEF DESCRIPTION OF THE FIGURES

Other characteristics and advantages of the invention will be more apparent from a reading of the following description of an embodiment and variants provided merely by way of a simple illustrative and non-limiting example, and the appended drawings, among which.

DETAILED DESCRIPTION OF THE EMBODIMENTS

Figure 1:
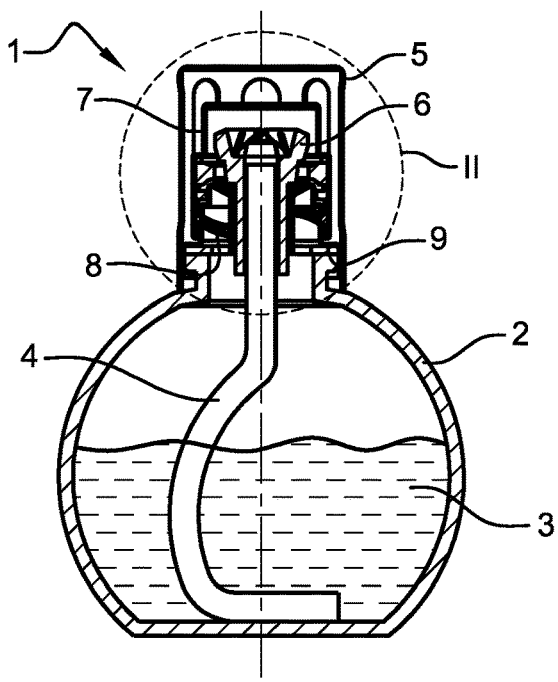
FIG. 1 is a view in cross section of a device for the diffusion of a fragrance or active substance by catalysis according to one embodiment of the invention.

With reference to FIG. 1, a device for the diffusion of a fragrance or active substance by catalysis 1 according to some of the embodiments is described below.

The device for the diffusion of a fragrance or active substance by catalysis 1 according to some of the embodiments includes a bottle 2 intended to contain a quantity of liquid 3. The liquid 3 includes a fragrance or active substance in the form of molecules of that fragrance or active substance mixed in a suitable solvent. Such a liquid for a device for the diffusion of a fragrance or active substance by catalysis 1 according to some of the embodiments is in itself known. At a neck of the bottle 2 the device for the diffusion of a fragrance or active substance by catalysis 1 according to some of the embodiments includes a base 8 mounted on the neck of the bottle with a seal 9. At a top of the base 8 the device for the diffusion of a fragrance or active substance by catalysis 1 according to some of the embodiments includes a catalytic combustion burner 6. The burner is fitted onto one extremity of a capillary wick 4, whose other extremity is immersed in liquid 3 contained in bottle 2. In order to close the device for the diffusion of a fragrance or active substance by catalysis 1 according to some of the embodiments the latter further includes a cap 7 removably mounted on the base 8 so as to cover the burner 6. Finally the device for the diffusion of a fragrance or active substance by catalysis 1 according to some of the embodiments includes a pierced hood 5 protecting the burner 6 when the device for the diffusion of a fragrance by catalysis 1 according to some of the embodiments is in operation.

Figure 2:
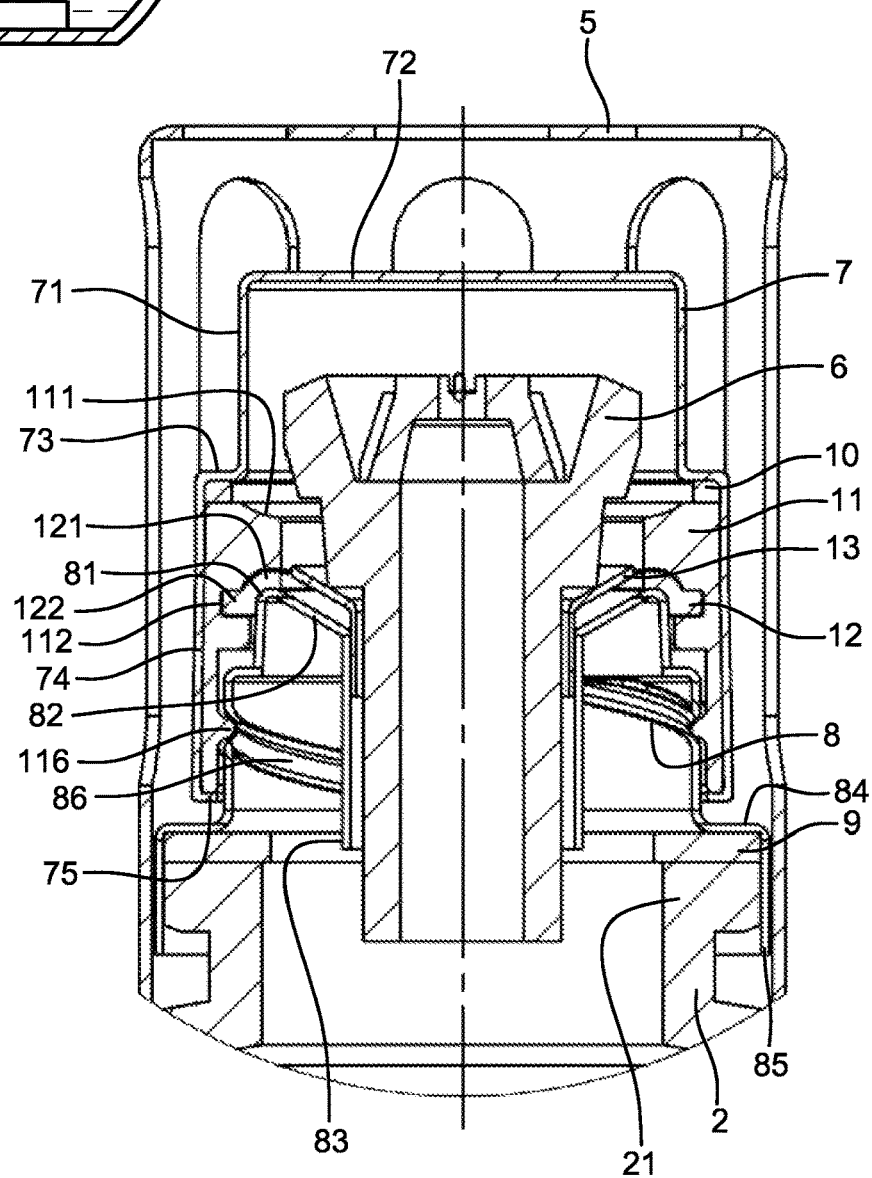
FIG. 2 is a view in cross section of detail II in FIG. 1.

With reference to FIG. 2, the head of the device for the diffusion of a fragrance or active substance by catalysis 1 according to some of the embodiments in greater detail is described below.

The base 8 is attached to neck 21 of bottle 2. The base 8 includes a shoulder 84 which rests against an annular seal 9 fitted between this shoulder 84 and an upper surface of neck 21 of bottle 2. One extremity 85 of the base 8 is then folded back on neck 21 of bottle 2. The shoulder 84 is surmounted by a first part which is cylindrical in revolution including a thread 86, then by a second part which is cylindrical in revolution having a diameter which is smaller than a diameter of the first part which is cylindrical in revolution. The second part which is cylindrical in revolution terminates in a top 81 having a periphery which is here radially external and therefore located at a right angle to a wall of the second part which is cylindrical in revolution. The top 81 is of a convex rounded shape. The base 8 has a frustoconical part 82 starting from the top 81 and extending toward the interior of the base 8 to join a third part 83 which is cylindrical in revolution and coaxial with the first and second parts which are cylindrical in revolution. A lower extremity of the third part 83 which is cylindrical in revolution extends into the bottle 2. Thus if liquid 3 is present on the frustoconical part it will flow by gravity along this frustoconical part 82 toward the interior and then along the third part 83 which is cylindrical in revolution to finally fall back into the bottle 2.

The base 2 is here made by deforming a thin metal sheet such as aluminum or an alloy thereof.

The head of the device for the diffusion of a fragrance or active substance by catalysis 1 according to some of the embodiments include a cap 7 removably mounted on base 8. Cap 7 is of a general shape which is cylindrical in revolution and includes a lower part 74 ending in a re-entrant flange 75 and an upper part 71 ending in a flat surface 72 which closes off the shape which is cylindrical in revolution of cap 7 from above. In the embodiment illustrated in FIG. 2, the lower part 74 is connected to the upper part 71 through a shoulder 73 because the two parts, the lower 74 and upper 71, do not have the same diameter; the upper part 71 has a smaller diameter than lower part 74. The upper part 71 and lower part 74 are made from the same thin deformed sheet of heat-resistant material as the base 8. This sheet of heat-resistant material is of metal or aluminum or an alloy of the latter, depending upon the distance between the sheet of heat-resistant material and the burner. As a variant, the upper part 71 and lower part 74 are manufactured from a thermoplastic if the distance between the cap and the burner allows it. The assembly thus forms a cover of heat-resistant material.

The cap 7 further includes an insert 11 which is fitted into lower part 74 of cap 7. The insert 8 is held within cap 7 by the re-entrant flange 75 at the bottom and at the top by the shoulder 73 through the intermediary of a first seal 10. This first seal 10 prevents any leaks of liquid 3 between the metal part of the cap 7 and the insert 11. The insert 11 is of a shape which is cylindrical in revolution and is hollow from an upper extremity to a lower extremity. From the upper extremity the insert includes a concave circular opening 111 in the form of a cup, then a neck including a circular groove 112, then a threaded part 116. The threaded part 116 is intended to fit with the thread 86 of the base 8 to hold the cap 7 in place on the head of the device for the diffusion of a fragrance by catalysis 1 according to the invention as illustrated in FIG. 2. The insert 11 is made of a plastics material which is resistant to heat, such as a thermoplastic, and resistant to the liquid 3 used.

Groove 112 houses a second seal 12. Second seal 12 is of annular shape and includes a convex radially inner part 121 in the form of a rounded hat and a radially outer part 112 forming a horizontal flange. The groove 112 has a shape which complements the horizontal flange 122 and an upper surface of the radially inner part 121. Thus when the cap 7 is mounted on the base 8, a lower surface of the radially inner part 121 rests on and complements the rounded top 81 of the base 8 whose shape complements the lower surface of the radially inner part 121 of the second seal 12. Once the cap 7 has been screwed onto the base 8 a volume is bounded by the upper part 71 of cap 7, the first seal 10, an upper part of the insert 11 and second seal 12. This volume houses the burner head 6 and is sealed in relation to the exterior; thus, if the device for the diffusion of a fragrance or active substance by catalysis 1 according to some of the embodiments is overturned or placed in a horizontal position liquid 3 then flows within said volume and remains confined therein because of the seal provided. Once the device for the diffusion of a fragrance or active substance by catalysis 1 according to some of the embodiments has been restored to its vertical position of use, the liquid 3 present in said volume returns into the enclosure of the bottle 2 flowing by gravity along the frustoconical part 82 of the base 8 toward the interior and then along the third part 83 which is cylindrical in revolution of the base 8 to finally fall back into the bottle 2. Thus, a user can then remove the cap 7 and light the burner without danger.

As illustrated in FIG. 2, the burner 6 is slipped into the base 8 and retained by the latter. It is here positioned in a burner support 13 which acts as an interface between the burner 6 and the base 8. The burner 6 and the burner support 13 are not further described herein because they are in themselves well known to those with sufficient skill in the art. The same applies to the pierced protection 5. It should be noted that once the device for the diffusion of a fragrance or active substance by catalysis 1 according to some of the embodiments is restored to its vertical position of use part of the liquid can also flow between the burner support 13 and the burner 6 toward the enclosure of bottle 2.

Figure 3:
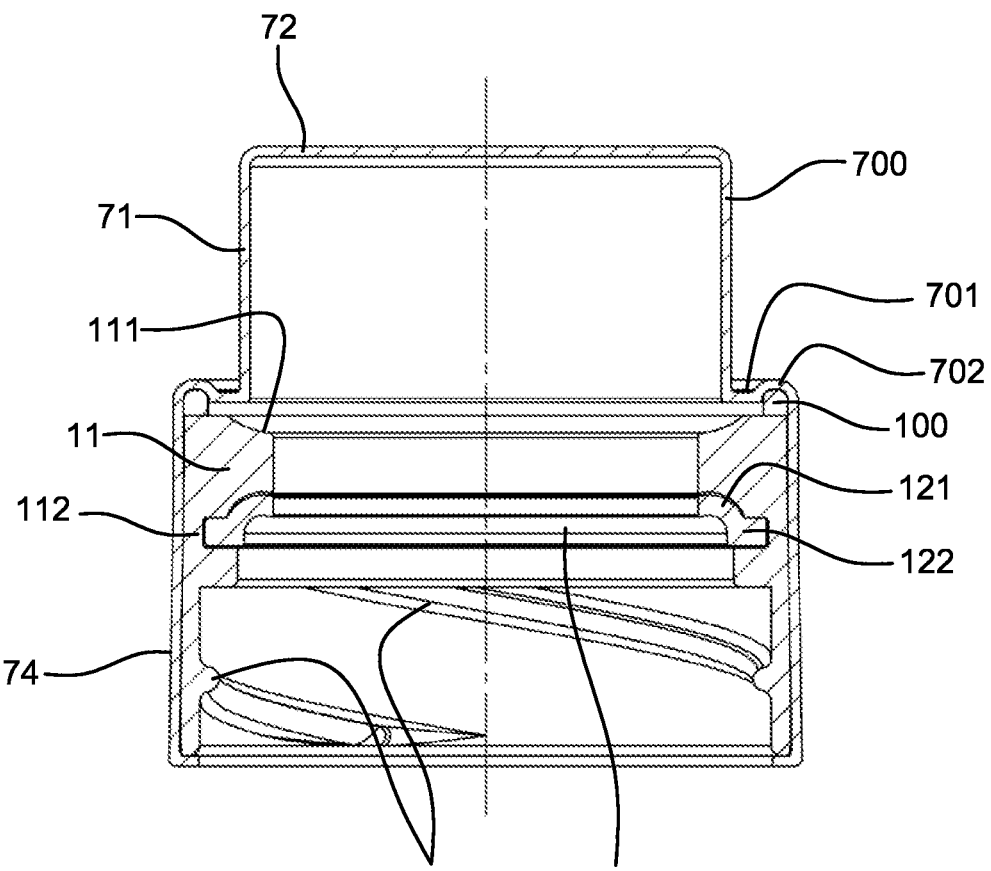
FIG. 3 is a view in cross section of a variant embodiment of the cap for a device according to the invention.

With reference to FIG. 3, a first variant embodiment of a cap 700 of the device is described for the diffusion of a fragrance or active substance by catalysis 1 according to some of the embodiments. The cap 700 only differs from the previously described cap 7 in the part connecting the lower part 74 to the upper part 71; it includes a horizontal annular rim 71 surrounded by a convex boss 702 which is also annular. Internally the boss 702 forms a groove to receive a variant embodiment 100 of the first seal. The other elements of cap 700 are identical to those of the cap 7 and will not be described again. The cap 700 includes the previously described insert 11.

Figure 4:
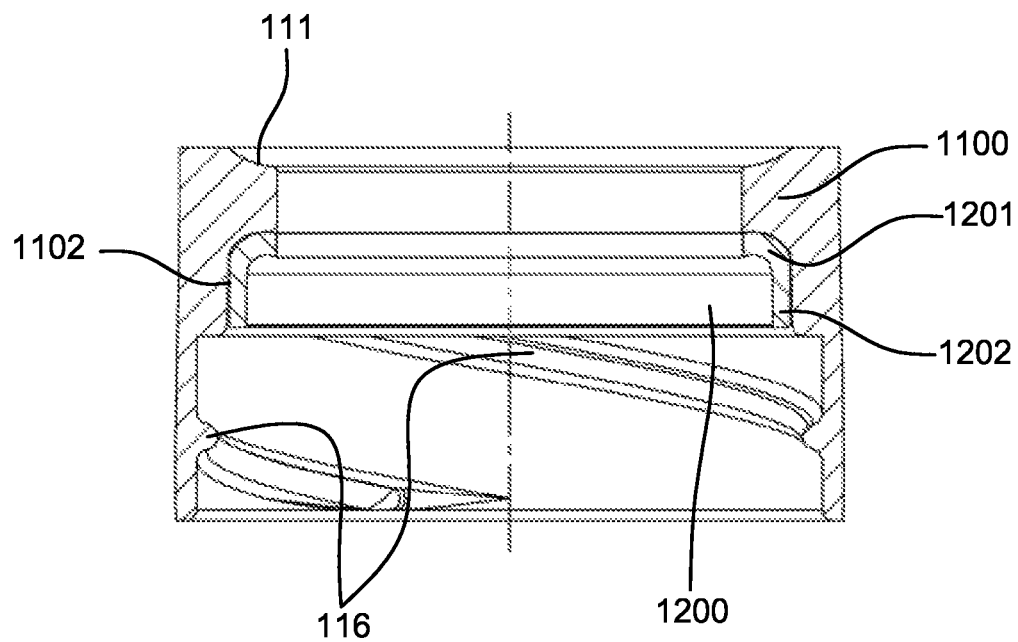
FIG. 4 is a view in cross section of a variant embodiment of the insert for a cap in FIG. 2 or 3.

With reference to FIG. 4, a variant embodiment of an insert 1100 and a second seal 1200 is described below.

The insert 1100 may also be mounted in both the cap 7 and cap 700. The insert 1100 differs from the previously described insert 11 in that the groove 112 is replaced by a hollow recess 1102 in the form of an upside-down cup. The second seal 1200 is of a complementary shape and includes a wall 1202 which is cylindrical in revolution surmounted by an upper convex part 1201 in the form of a rounded hat, similar to the convex radially inner part 121 in the form of a rounded hat of the previously described second seal 12. When this insert 1100 mounted in a cap 7 or 700 is used, the inner surface of second seal 1200 rests on and complements the rounded top 81 of the base, the wall 1202 which is cylindrical in revolution coming into contact with an outer radially lateral surface of a radially outer wall of base 8 located beneath the top 81.

Figure 5:
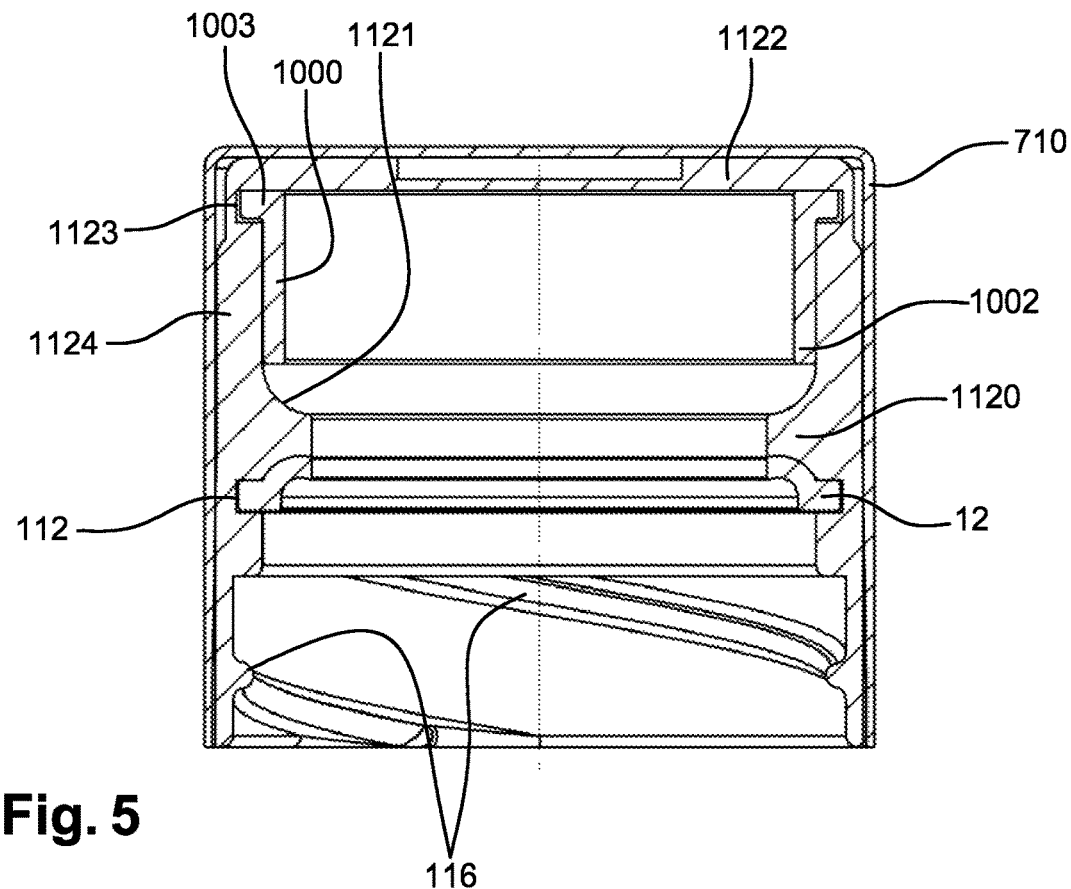
FIG. 5 is a view in cross section of a second variant embodiment of the cap for the device according to the invention.

With reference to FIG. 5, a second variant embodiment of the cap 710 for a device for the diffusion of a fragrance or active substance by catalysis 1 according some of the embodiments is described below.

The cap 710 includes an upper part which lies in the extension of the upper part without a part connecting the two, because the lower and upper parts have the same diameter. The cap 710 has an insert 1120, a lower part of which is identical to the previously described insert 11 (as a variant, this lower part may be similar to previously described insert 1100). The insert 1120 includes a concave cup 1121 of shape similar to the concave circular opening 111 of the insert 11. Here this cup 1121 is extended upward by a wall 1124 which is cylindrical in revolution and closed off at the top by a horizontal wall 1122. An inner groove 1123 is located beneath horizontal wall 1122 in wall 1124 which is cylindrical in revolution. A sleeve 1000 is fitted in groove 1123. For this purpose, it has a rim 1003 which is housed in grove 1123. The sleeve 1000 includes a wall 1002 which is cylindrical in revolution and extends the opposite wall 1124 which is cylindrical in revolution and is in contact therewith. The use of this variant embodiment of the cap 710 is identical to the previous uses of caps 7 and 700.

Figure 6:
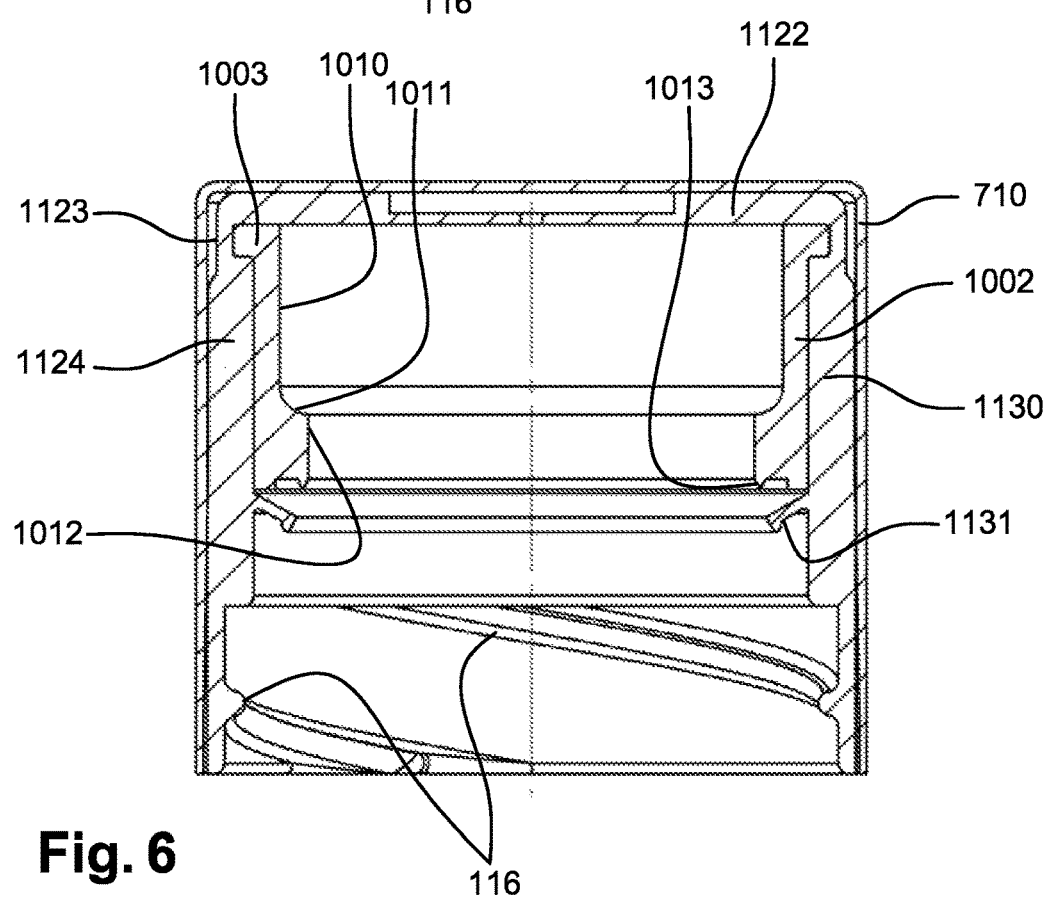
FIG. 6 is a view in cross section of a third variant embodiment of the cap for the device according to the invention.

A variant embodiment of the insert 1130 intended for the cap 710 of the device for the diffusion of a fragrance or active substance by catalysis 1 according to some of the embodiments illustrated in FIG. 6 is described below.

In this variant embodiment, the insert 1130 includes a lower part including a thread 116 intended to act together with the thread 86 of the base 8. Above this thread 116 the insert 1130 includes a deformable sealing lip 1131 of annular shape extending so as to project centripetally toward the interior. Above this sealing lip 1131 the insert includes a wall 1124 which is cylindrical in revolution and ends in an inner groove 1123 surmounted by a horizontal closing wall 1122. A sleeve 1010 is fitted in groove 1123. For this purpose sleeve 1010 includes a rim 1003 which is housed in groove 1123.

The sleeve 1010 includes a wall 1002 which is cylindrical in revolution and extends opposite the wall which is cylindrical in revolution of insert 1130 and is in contact therewith. The wall 1002 which is cylindrical in revolution of sleeve 1010 extends downward via a concave rim 1011 in the form of a cup and then a second wall 1012 which is cylindrical in revolution. At a lower extremity of the second wall 1012 which is cylindrical in revolution the sleeve 1010 includes an annular stop 1013.

When the cap 710 including the insert 1130 is screwed onto the base 8 the sealing lip 1131 rests against the rounded top 81 of the insert 8. As screwing continues, the sealing lip 1131 deforms as a result of bearing against the top 81 until it comes into contact with the annular stop 1013 of sleeve 1010. The seal is thus made between the sealing lip 1131 and the base 8.

Figure 7:
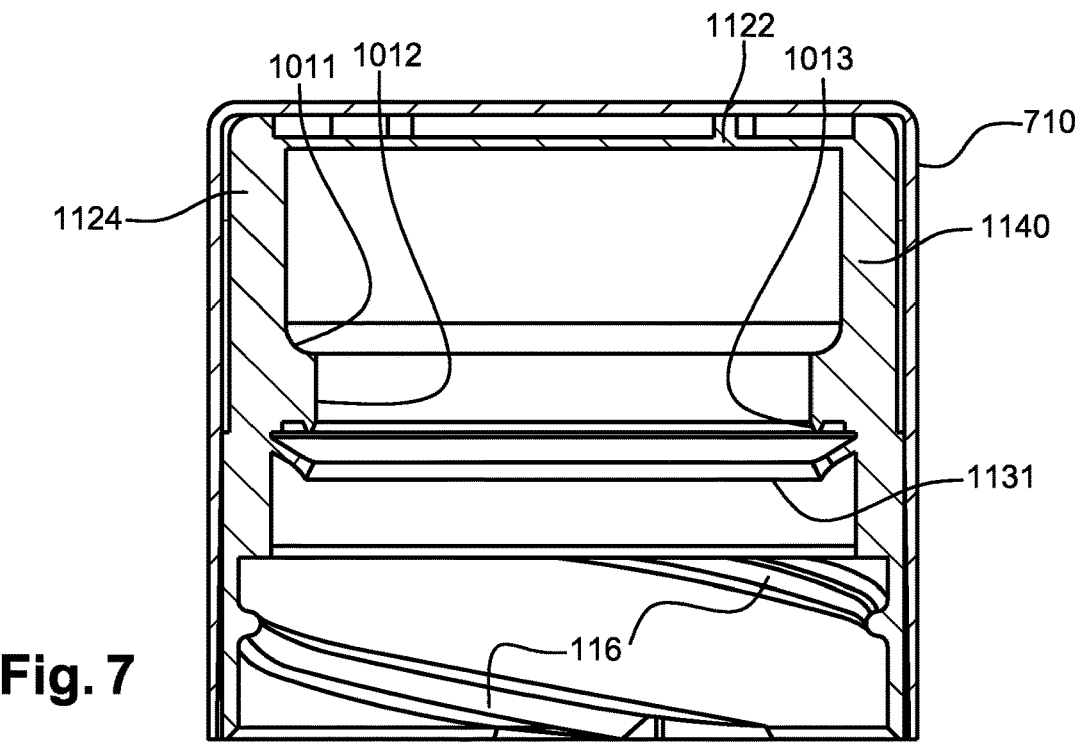
FIG. 7 is a view in cross section of a variant embodiment of the cap in FIG. 6; and, FIG. 8 is a view in cross section of a fourth variant embodiment of the cap for the device according to the invention.

FIG. 7 illustrates a variant embodiment 1140 of the previous insert intended for a cap 710 of the device for the diffusion of a fragrance or active substance by catalysis 1 according to some of the embodiments. The insert 1140 of this variant embodiment differs from the previous one illustrated in FIG. 6 in that the insert 1140 includes the previous insert 1130 and the sleeve 1010 in an integrated way so as to form a single piece of the same material. The other characteristics are the same.

Figure 8:
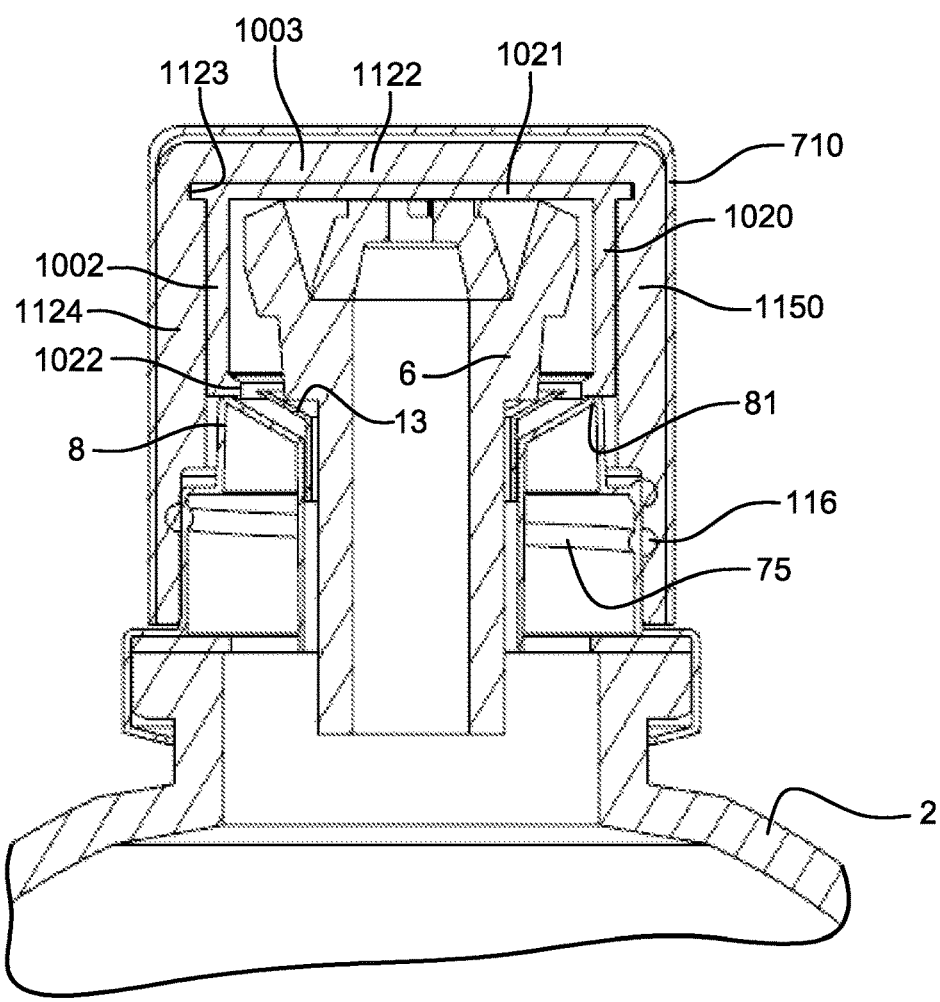

With reference to FIG. 8, another variant embodiment of a insert 1150 intended for cap 710 of the device for the diffusion of a fragrance or active substance by catalysis 1 according to some of the embodiments is described below.

In this variant embodiment, the insert 1150 includes a lower part including a thread 116, intended to act together with the thread 86 of the base 8. Above this thread 116 the insert 1150 includes a wall 1124 which is cylindrical in revolution and ends in an inner groove 1123 surmounted by a horizontal closing wall 1122. A sleeve 1020 is mounted in the groove 1123. For this purpose the sleeve 1020 includes a rim 1003 which is housed in the grove 1123. In the plane of the rim 1003 the sleeve 1020 includes a horizontal closing wall 1021 extending opposite and in contact with horizontal wall 1122 of insert 1150. The sleeve 1020 includes a wall 1002 which is cylindrical in revolution and extends the opposite wall 1124 which is cylindrical in revolution of the insert 1150 and is in contact therewith. The wall 1002 which is cylindrical in revolution of sleeve 1020 ends toward the bottom at a lower extremity in an annular centripetal rim 1022 which forms a sealing lip.

When the cap 710 including the insert 1150 is screwed onto the base 8, the annular rim 1022 rests against rounded the top 81 of the base 8. A seal is thus provided between the annular rim 1022 and the base 8. Also, as it is screwed, the horizontal wall 1021 of the sleeve 1020 rests against the top of burner 6, as illustrated in FIG. 8.

In all the embodiments which have been described, the insert may be mounted in the cap in one of the following ways:

the insert is adhesively bonded in the cap;
the insert is forced into the cap;
the cap is crimped with the insert.

As a variant embodiment the cap and the insert have ribs to prevent any rotational movement of one with respect to the other once they have been mounted.

As an additional variant embodiment, in the situation where the cap is made of a thermoplastic, the insert is of the same material as the cap, thus forming a single continuous piece.

Of course many modifications may be made to the invention without thereby going beyond its scope.

The invention claimed is:

1. A device for the diffusion of a fragrance or active substance by catalysis, comprising:
   a bottle including a base, and containing a liquid including a fragrance or an active substance, the base defining a radial axis and including a cylindrical part which terminates at a top of the base having a periphery being radially external and located at the right angle to a wall of the cylindrical part,
   a catalytic combustion burner mounted on the base,
   a capillary wick attached to the burner and partly immersed in the liquid, and
   a closing cap configured to be removable and is mounted on the base and covering the burner, wherein that the cap includes sealing means bearing against the periphery of the top of the base.

2. The device according to claim 1, wherein the sealing means include a seal having a shape which complements the periphery of the top of the base.

3. The device according to claim 2, wherein the cap includes a housing for receiving and holding the seal.

4. The device according to claim 1, wherein the sealing means comprise a sealing lip bearing against the periphery of a top of the base.

5. The device according to claim 1, wherein that the cap includes a cover made of heat-resistant material.

6. The device according to claim 5, wherein the cap includes an insert fitted into the cover of heat-resistant material.

7. The device according to claim 6, wherein the insert is hollow and extends from below a burner head toward the bottle.

8. The device according to claim 5, wherein the cover includes a shouldered flange.

9. The device according to claim 7, wherein the cap includes a sealing element between an upper surface of the insert and the cover of heat-resistant material.

10. The device according to claim 1, wherein it includes a burner support positioned between the burner and the base.

* * * * *